United States Patent [19]

Kellner et al.

[11] Patent Number: 5,523,501
[45] Date of Patent: Jun. 4, 1996

[54] CATALYTIC HYDROGENOLYSIS

[75] Inventors: Carl S. Kellner; V. N. Mallikarjuna Rao, both of Wilmington, Del.; Allen C. Sievert, Elkton, Md.

[73] Assignee: E. I. Du Pont de Nemours and Company, Wilmington, Del.

[21] Appl. No.: 362,331

[22] Filed: Dec. 22, 1994

[51] Int. Cl.⁶ ................................................ C07C 17/10
[52] U.S. Cl. ................................................ 570/176
[58] Field of Search ................................................ 570/176

[56] References Cited

U.S. PATENT DOCUMENTS

| | | | |
|---|---|---|---|
| 2,942,036 | 6/1960 | Smith et al. | 260/653 |
| 4,319,060 | 3/1982 | Cunningham et al. | 570/177 |
| 5,136,113 | 8/1992 | Rao | 570/176 |
| 5,157,171 | 10/1992 | Seivert et al. | 570/151 |
| 5,315,048 | 5/1994 | Van Der Puy et al. | 570/176 |

FOREIGN PATENT DOCUMENTS

| | | |
|---|---|---|
| 0347830 | 12/1989 | European Pat. Off. . |
| 1-128942 | 5/1989 | Japan . |
| WO92/20440 | 9/1994 | WIPO . |

OTHER PUBLICATIONS

Gervasutti, C. et al "Hydrogenolysis of Dichlorotetrafluoroethane Isomeric Mixtures for the Formation of 1,1,3–Tetrafluoroethane", *J. of Fluorine Chem.*, 19, 1–20(1981/1982).

Biswas, M. et al "Vinyl Polymerization by Carbon Black. II. Modification of Carbon Black and Its Use in the Polymerization of N–Vinylcarbazole", *J. Bacromol. Sci.–Chem.*, A20(8), 861–876 (1983).

Goleva, A. A. et al, "Catalytic Dehydrochlorination of Chlorethanes. II. Catalytic Dehydrochlorination of 1,1,2,2–Tetrachloroethane", *Russian J. of Phys. Chem.*, 44(2), 290–291 (1970).

Onoda, Takeru et al., *Aliphatics*, 80, p. 389, Abstract No. 145469w (1974).

Onoda, Takeru et al, *Aliphatics*, 80, p. 389, Abstract No. 145470q (1974).

*Primary Examiner*—Alan Siegel

[57] ABSTRACT

A process is disclosed for the catalytic hydrogenolysis of at least one starting material selected from saturated acyclic halofluorocarbons and hydrohalofluorocarbons containing three or four carbon atoms, and from one to five non-fluorine halogens (each non-fluorine halogen being independently chlorine or bromine) wherein all non-fluorine halogen substituents are contained on end carbons. The process involves reacting the starting material with hydrogen at an elevated temperature of about 300° C. or less in the presence of a catalyst containing a catalytically effective amount of palladium supported on carbon to produce a hydrogenolysis product wherein over 80 mole percent of the hydrogenolysis product is a saturated compound having the same distribution of fluorine substituents as the starting material. The carbon support has an ash content of less than about 0.5% by weight.

7 Claims, No Drawings

1

CATALYTIC HYDROGENOLYSIS

FIELD OF THE INVENTION

This invention relates to catalytic hydrogenolysis of halofluorocarbons and hydrohalofluorocarbons, and more particularly, to the hydrogenolysis of said materials using palladium-containing catalysts.

BACKGROUND

Various processes for the catalytic hydrogenolysis of chlorofluorocarbons and hydrochlorofluorocarbons are known. For example, U.S. Pat. No. 2,942,036 discloses the reaction of 1,2,2-trichloropentafluoropropane with hydrogen in the presence of palladium on activated carbon catalyst to produce 1,2,2-trihydropentafluoropropane. The examples show that under the conditions of the experiments one of the products from this reaction is $CF_3CH=CF_2$. The carbon support may be treated with aqueous HF prior to depositing palladium on the support for the purpose of removing silica from the carbon. U.S. Pat. No. 5,315,048 discloses a process wherein 1,2,3-trichloropentafluoropropane is contacted with hydrogen in the presence of palladium on alumina to produce 1,1,1,2,3-pentafluoropropane. It is mentioned in this patent that reduction of 1,2,3-trichloropentafluoropropane with hydrogen over Pd on carbon gives primarily a mixture of $HCF_2CHFCF_2H$ and $HCF_2CHFCF_2Cl$. U.S. Pat. No. 4,319,060 discloses a process wherein 1,1-dichlorotetrafluoroethane contained in mixtures thereof with 1,2-dichlorotetrafluoroethane is selectively degraded to provide 1,2-dichlorotetrafluoroethane substantially free of 1,1-dichlorotetrafluoroethane. The process includes contacting, in the vapor phase, an organic feed composition containing a major amount of the 1,2-isomer and a minor amount of the 1,1-isomer with hydrogen in the presence of a hydrodechlorination catalyst. C. Gervasutti et al., J. Fluorine Chem., 19, 1–20 (1981/2) report that 1,1,1,2-tetrafluoroethane was prepared from isomeric mixtures of dichlorotetrafluoroethanes through selective hydrogenolysis of the $CF_3CCl_2F$ isomer present in the mixture catalyzed by Pd/C. The other isomer $CClF_2CClF_2$ appeared more stable to hydrogenolysis and was only converted partially to the monohydrogenated derivative $CHF_2CClF_2$.

U.S. Pat. No. 5,136,113 discloses catalytic hydrogenolysis of fluorohalocarbons and fluorohalohydrocarbons using catalysts of certain metals (e.g., palladium) on low-ash carbon. Various other processes using catalysts containing acid-washed carbon have been studied. A. A. Goleva et al., Russ. J. Phys. Chem., 442, 290–1 (1970) discloses the dehydrochlorination of 1,1,2,2-tetrachloroethane to the olefin trichloroethylene (and HCl) using activated charcoal as the catalyst. Activated charcoal treated with hydrochloric acid proved to be more active than an untreated specimen for the production of trichloroethylene.

SUMMARY OF THE INVENTION

The present invention provides a process for the catalytic hydrogenolysis of at least one starting material selected from acyclic saturated halofluorocarbons and hydrohalofluorocarbons containing three or four carbon atoms, and from one to five non-fluorine halogens, wherein each non-fluorine halogen is independently selected from the group consisting of chlorine and bromine and wherein all non-fluorine halogen substituents are contained on end carbons (i.e., the first and/or the third carbons of three-carbon compounds and the first and/or fourth carbons of four-carbon compounds). The process comprises reacting said starting material with hydrogen at an elevated temperature of about 300° C. or less in the presence of a catalyst containing a catalytically effective amount of palladium supported on carbon to produce a hydrogenolysis product wherein over 80 mole percent of the hydrogenolysis product is a saturated compound having the same distribution of fluorine substituents as the starting material, said carbon support having an ash content of less than about 0.5% by weight.

DETAILED DESCRIPTION

The catalysts suitable for the process of this invention comprise palladium and may optionally contain additional Group VIII metals (e.g., Pt, Ru, Rh or Ni). The palladium is supported on low-ash carbon. The palladium-containing material used to prepare the catalysts is preferably a palladium salt (e.g., palladium chloride). The other metals, when used, may be added to the support in the conventional manner (e.g., as a soluble salt of the metal).

The concentration of palladium supported on low-ash carbon is typically within the range of from about 0.2% to about 5% by weight based on the support. The concentration of additional Group VIII metal, when used, is about 3% by weight, or less, based on the support; but palladium is ordinarily at least 50% by weight of the supported metal (preferably at least 80% by weight of the total metals present on the support).

Low-ash carbon supports can be prepared by a variety of methods. One method is to wash the carbon support with acid prior to deposit of metal. Acid treatment can be performed with more than one acid, but the initial acid treatment typically uses an acid other than hydrofluoric acid. Preferred acids used for the initial acid treatment contain neither phosphorus nor sulfur. Examples of acid that can be used in the initial acid treatment include organic acids such as acetic acid and inorganic acids such as hydrochloric acid or nitric acid. Preferably hydrochloric acid is used. The second acid treatment, when employed, advantageously uses hydrofluoric acid. Normally, the carbon is treated with acid such that after such treatment, the carbon contains less than about 0.5% by weight ash and preferably less than about 0.3% by weight ash. Vegetable-based carbons, such as coconut shell based carbon are preferred for the acid treatment. A preferred embodiment is described below.

A carbon support is soaked overnight with gentle stirring in a 1 molar solution of the acid prepared in deionized water. The carbon support is then separated and washed with deionized water or until the pH of the washings is about 3. Preferably, the carbon support is then soaked again with gentle stirring in a 1 molar solution of the acid prepared in deionized water for 12 to 24 hours. The carbon support is then washed with deionized water until the washings are substantially free of the anion of the acid (e.g., $Cl^-$ or $NO_3^-$), when tested by standard procedures. The carbon support is then separated and dried at 120° C. If necessary, the washed carbon is then soaked in 1 molar HF prepared in deionized water for about 48 hours at room temperature with occasional stirring. The carbon support is separated and washed with deionized water until the pH of the washings is greater than 4. The carbon support is then dried at 150° C. in air followed by calcination at 300° C. for about 3 hours in air prior to its use as a support. Reference is made to U.S. Pat. No. 5,136,113 for further details relating to producing acid-washed carbon catalysts.

The present invention provides high selectivity to product compounds having the same distribution (i.e., the same number and the same relative position) of fluorine substituents as the starting compound. The invention includes the hydrogenolysis of chlorofluorocarbons which contain three carbons and no more than four chlorines in the molecule (e.g., $CCl_3CF_2CClF_2$, $CCl_2FCF_2CCl_2F$, $CCl_2FCF_2CClF_2$, $CCl_3CF_2CF_3$, $CCl_2FCF_2CF_3$, $CClF_2CF_2CClF_2$ and $CClF_2CF_2CF_3$). This invention also includes the hydrogenolysis of hydrochlorofluorocarbons which contain three carbons and (i) no more than three chlorines and one hydrogen in the molecule (e.g., $CHCl_2CF_2CClF_2$, $CHClFCF_2CCl_2F$, $CCl_2FCF_2CHF_2$, $CCl_3CF_2CHF_2$, $CHClFCF_2CClF_2$, $CHCl_2CF_2CF_3$, $CHF_2CF_2CClF_2$ and $CHClFCF_2CF_3$); (ii) two chlorines and two hydrogens in the molecule (e.g., $CHClFCF_2CHClF$, $CHCl_2CF_2CHF_2$ and $CClF_2CF_2CH_2Cl$); (iii) one chlorine and two hydrogens in the molecule (e.g., $CHClFCF_2CHF_2$, $CH_2FCF_2CClF_2$ and $CH_2ClCF_2CF_3$); or (iv) one chlorine and three hydrogens in the molecule (e.g., $CH_2ClCF_2CHF_2$, $CH_2FCF_2CHClF$ and $CH_3CF_2CClF_2$). This invention further includes the hydrogenolysis of chlorofluorocarbons containing four carbons and no more than five chlorines in the molecule (e.g., $CClF_2CF_2CF_2CClF_2$ and $CCl_2FCF_2CF_2CF_3$) and the hydrogenolysis of hydrochlorofluorocarbons which contain four carbon atoms and no more than four chlorines and one hydrogen in the molecule (e.g., $CClF_2CF_2CF_2CHF_2$, $CHClFCF_2CF_2CF_3$ and $CClF_2CF_2CHFCF_3$). The valencies not satisfied by chlorine or hydrogen are satisfied by fluorine. Of note are embodiments where both end carbons contain non-fluorine halogen. Also of note are embodiments where only one carbon contains non-fluorine halogen.

Use of suitable temperatures, contact times and intermediate recycle (where applicable) in accordance with this invention can result in production of hydrogenolysis product wherein all chlorines of a starting material have been replaced by hydrogen, with high selectivity (i.e., over 80 mole percent based on the amount of starting material converted). For example, the present invention provides a process for reacting $CCl_2FCF_2CClF_2$ with hydrogen to produce $CH_2FCF_2CHF_2$ with high selectivity; a process for reacting $CCl_3CF_2CF_3$ with hydrogen to produce $CH_3CF_2CF_3$ with high selectivity; a process for reacting $CCl_2FCF_2CF_3$ with hydrogen to produce $CH_2FCF_2CF_3$ with high selectivity; a process for reacting $CClF_2CF_2CClF_2$ with hydrogen to produce $CHF_2CF_2CHF_2$ with high selectivity; a process for reacting $CClF_2CF_2CF_2CClF_2$ with hydrogen to produce $CHF_2CF_2CF_2CHF_2$ with high selectivity; a process for reacting $CHF_2CF_2CF_2CClF_2$ with hydrogen to produce $CHF_2CF_2CF_2CHF_2$ with high selectivity; a process for reacting $CCl_3CF_2CClF_2$ with hydrogen to produce $CH_3CF_2CHF_2$ with high selectivity; a process for reacting $CCl_2FCF_2CCl_2F$ with hydrogen to produce $CH_2FCF_2CH_2F$ with high selectivity; a process for reacting $CClF_2CF_2CF_3$ with hydrogen to produce $CHF_2CF_2CF_3$ with high selectivity; a process for reacting $CHCl_2CF_2CClF_2$ with hydrogen to produce $CH_3CF_2CHF_2$ with high selectivity; a process for reacting $CHClFCF_2CCl_2F$ with hydrogen to produce $CH_3CF_2CHF_2$ with high selectivity; a process for reacting $CCl_3CF_2CHF_2$ with hydrogen to produce $CH_3CF_2CHF_2$ with high selectivity; a process for reacting $CHClFCF_2CClF_2$ with hydrogen to produce $CH_2FCF_2CHF_2$ with high selectivity; a process for reacting $CCl_2FCF_2CHF_2$ with hydrogen to produce $CH_2FCF_2CHF_2$ with high selectivity; a process for reacting $CHCl_2CF_2CF_3$ with hydrogen to produce $CH_3CF_2CF_3$ with high selectivity; a process for reacting $CHF_2CF_2CClF_2$ with hydrogen to produce $CHF_2CF_2CHF_2$ with high selectivity; a process for reacting $CHClFCF_2CF_3$ with hydrogen to produce $CH_2FCF_2CF_3$ with high selectivity; a process for reacting $CCl_2FCF_2CF_3$ with hydrogen to produce $CH_2FCF_2CF_3$ with high selectivity; and a process for reacting $CHClFCF_2CF_2CF_3$ with hydrogen to produce $CH_2FCF_2CF_2CF_3$ with high selectivity. Mixtures of starting materials may also be used. For example, a mixture of $CCl_2FCF_2CF_3$ and $CClF_2CF_2CClF_2$ may be reacted with hydrogen to produce a mixture of $CHF_2CF_2CHF_2$ and $CH_2FCF_2CF_3$ with high selectivity.

The present invention also provides a process for a selective two-step hydrogenolysis of a mixture of $CCl_2CF_2CF_3$ and $CClF_2CF_2CClF_2$ (e.g., in a ratio of from 1:9 to 9:1). In the first step of the two-step process the $CCl_2FCF_2CF_3$ is selectively reacted with hydrogen at a temperature less than about 200° C. to provide a mixture containing $CH_2FCF_2CF_3$ and $CClF_2CF_2CClF_2$. In the second step the $CClF_2CF_2CClF_2$ is reacted with hydrogen at a temperature greater than about 200° C. to provide $CHF_2CF_2CHF_2$. It is ordinarily preferable to recover the $CH_2FCF_2CF_3$ of the first step prior to carrying out the second step. Typically, the first step produces some $CHClFCF_2CF_3$ and $CF_2ClCF_2CHF_2$; and these may be included in the second step reactants. The product from both steps of the reaction are essentially saturated compounds containing the same number of fluorine atoms as the respective initial starting compound and contains less than 10% of olefinic co-product and product containing less fluorine than the initial starting materials.

The hydrogenolysis of the present invention is conducted at an elevated temperature. Ordinarily the temperature is about 300° C. or less. Typically, satisfactory reaction rates are achieved at operating temperatures of about 150° to 250° C. Generally, in order to provide substantial hydrogenolysis product yields, the amount of hydrogen used is at least about 0.5 mole per mole of the organic starting material. To provide yields desired in many embodiments, at least stoichiometric amounts of hydrogen are used. A considerable excess of hydrogen can also be advantageously employed to provide the yields desired in many embodiments in addition to serving as a heat sink to reduce the overall temperature rise in the reactor.

Pressure is not critical. Atmospheric and superatmospheric pressures are the most convenient and are therefore preferred.

Practice of the invention will become further apparent from the following non-limiting examples.

EXAMPLE 1

Carbon Support

The carbon support used in the examples was a 4×8 mesh (about 4.7 mm×2.4 mm) commercial grade coconut shell carbon which had (before washing) an ash content of about 2.6 weight percent. After hydrochloric acid washing, the carbon support had an ash content of less than about 0.1 weight percent.

Preparation of an isomeric mixture of $CClF_2CF_2CClF_2$ and $CCl_2FCF_2CF_3$

A 400 mL Hastelloy™ nickel alloy shaker tube was charged with $CCl_3F$-modified anhydrous aluminum chloride (3.0 g) prepared as illustrated in U.S. Pat. No. 5,157,171. The tube was sealed, cooled to −78° C. and evacuated and purged with nitrogen. It was then charged with $CCl_2F_2$ (50 g, 0.41 mole). The cold shaker tube was placed in a barricade and charged with 25 g (0.25 mole) of tetrafluoroethylene. The reactor was warmed to 60° C. over the course of 15 minutes during which time the pressure rose to 80 psig (653 kPa). The temperature was maintained for an additional 1.3 hours at 60° C. and then raised to 80° C. and held for one hour at which time the pressure rose to 112–115 psig (873–894 kPa). After cooling and discharge there was obtained 54.7 g of a clear supernatant liquid. Analysis of this liquid by $^{19}$F NMR showed that the product contained 13.9% $CClF_2CF_2CClF_2$ and 53.5% $CCl_2FCF_2CF_3$ and other products. The product isomer mix was then recovered from this reaction mixture by distillation.

Hydrogenolysis of an isomeric mixture of $CClF_2CF_2CClF_2$ and $CCl_2FCF_2CF_3$ The starting material was prepared from two different runs by the procedure described above and combined for the hydrogenolysis experiment. They were present in the ratio of 41.3% $CClF_2CF_2CClF_2$ (CFC-216 ca) and 58.7% $CCl_2FCF_2CF_3$ (CFC-216 cb). This liquid isomeric mixture of CFC-216 ca and CFC-216 cb, 0.3 mL/minute, was vaporized and mixed with 300 cc/minute of hydrogen. This vaporized mixture was passed through a 1" O.D.×13" reactor (25.4 mm×330 mm) containing containing 46 g of 2 weight percent palladium supported on 4×8 mesh (4.7 mm×2.4 mm) low-ash, acid-washed carbon heated to 150° C. in a fluidized sand bath. About four hours after start of the reaction, organic product analysis using conventional gas chromatography indicated that $CCl_2FCF_2CF_3$ conversion was essentially complete with about 6% of $CClF_2CF_2CClF_2$ being converted to the monohydrogenolysis product (i.e., HCFC-226 cb or $CF_2ClCF_2CF_2H$).

The temperature of the reactor was then increased to 275° C. for a period of about four hours with the organic starting material and hydrogen flowing through the reactor. At the end of this period, the reactor temperature was brought back down to 150° C. After about eight hours of operation at 150° C., organic product analysis indicated that $CCl_2FCF_2CF_3$ conversion was still essentially complete, with about 70% selectivity to 1,1-dihydrohexafluoropropane (HFC-236 cb) and about 23% selectivity to 1-hydro-1-chlorohexafluoropropane (HCFC-226 ca). The conversion of $CClF_2CF_2CClF_2$ was essentially zero and products arising from loss of fluorine from the starting substrates was less than about 5%.

Comparative Hydrogenolysis of $CF_3CCl_2CF_3$

Liquid $CF_3CCl_2CF_3$, 3 mL/hour, was vaporized and mixed with 10 cc/minute of hydrogen. This vapor mixture was sent through a 0.5" O.D.×8" (12.7 mm×203 mm) Hastelloy™ nickel alloy reactor containing 7.2 g of 0.5 weight percent palladium supported on acid washed carbon maintained at 150° C. using a fluidized sand bath. Organic product analysis using conventional gas chromatography indicated that about 90% of the starting material had been converted. The hydrogen-containing products included 15.7% 2,2-dihydrohexafluoropropane (HFC-236 fa), 54.3% 2-chloro-2-hydrohexafluoropropane (HCFC-226 da), 12.3% 2-hydropentafluoropropene, and 1.7% 1,2,2-trihydropentafluoropropane (HFC-245 fa) and small quantities of other compounds.

This example was repeated except that the hydrogen flowrate was increased to 30 cc/minute. Organic product analysis using conventional gas chromatography indicated that the starting material conversion was essentially complete. The hydrogen-containing products included 24.8% 2,2-dihydrohexafluoropropane (HFC-236 fa), 54.6% 2-chloro-2-hydrohexafluoropropane (HCFC-226 da) and 19.8% 1,2,2-trihydropentafluoropropane (HFC-245 fa) and small quantities of other compounds.

This experiment illustrates that when using palladium supported on acid washed carbon as catalyst and where the two chlorines of the starting compound are on the internal carbon, an olefin and/or a saturated product containing one less fluorine than the starting compound can be produced in significant amounts.

EXAMPLE 2

$CHF_2CF_2CF_2CClF_2$ (HCFC-3281 cc)→$CHF_2CF_2CF_2CHF_2$ (HFC-338 pcc)

Liquid HCFC-3281 cc (2 mL/hr) was vaporized, mixed with hydrogen (10 cc/min) and sent through a 6"×0.5" (152 mm×12.7 mm) Hastelloy™ nickel alloy reactor containing 4.0 g of 0.3 wt % palladium on acid-washed carbon maintained at 275° C. in a fluidized sand bath. After about five hours of operation, organic product analysis using conventional gas chromatography indicated about 38% HCFC-3281 cc, 59% HFC-338 pcc, and small amounts of other products.

What is claimed is:

1. A process for the catalytic hydrogenolysis of a starting mixture of $CCl_2FCF_2CF_3$ and $CClF_2CF_2CClF_2$ comprising:

in a first step, selectively reacting the $CCl_2FCF_2CF_3$ with hydrogen at a temperature less than about 200° C. in the presence of a catalyst containing a catalytically effective amount of palladium supported on carbon, said carbon support having an ash content of less than about 0.5% to provide a mixture containing $CH_2FCF_2CF_3$ and $CClF_2CF_2CClF_2$; and in a second step, reacting the $CClF_2CF_2CClF_2$ with hydrogen at a temperature of about 300° C. or less and greater than about 200° C. in the presence of a catalyst containing a catalytically effective amount of palladium supported on carbon, said carbon support having an ash content of less than about 0.5% to provide $CHF_2CF_2CHF_2$; wherein over 80 mole percent of the hydrogenolysis product of said starting mixture is a saturated compound having the same distribution of fluorine substituents as $CCl_2FCF_2CF_3$ or $CClF_2CF_2CClF_2$.

2. The process of claim 1 wherein $CH_2FCF_2CF_3$ of the first step is recovered prior to carrying out the second step.

3. A process for the catalytic hydrogenolysis of a mixture of $CCl_2FCF_2CF_3$ and $CClF_2CF_2CClF_2$ in a ratio of from 1:9 to 9:1, comprising:

(1) selectively reacting $CCl_2FCF_2CF_3$ from said mixture with hydrogen at an elevated temperature of less than about 200° C. in the presence of a catalyst containing a catalytically effective amount of palladium supported on carbon to produce a hydrogenolysis product containing $CH_2FCF_2CF_3$ and $CClF_2CF_2CClF_2$ wherein over 80 mole percent of the hydrogenolysis product is a saturated compound having the same distribution of fluorine substituents as the starting material, said carbon support having an ash content of less than about 0.5% by weight; and (2) reacting said $CClF_2CF_2CClF_2$ at a temperature greater than about 200° C., and about 300° C. or less, in the presence of a catalyst containing a catalytically effective amount of palladium supported on carbon to provide hydrogenolysis product containing $CHF_2CF_2CHF_2$ wherein over 80 mole percent of the hydrogenolysis product is a saturated compound having the same distribution of fluorine substituents as the starting material, said carbon support having an ash content of less than about 0.5% by weight.

4. The process of claim 3 wherein $CH_2FCF_2CF_3$ from the hydrogenolysis product of (1) is recovered prior to (2).

5. The process of claim 3 wherein $CHClFCF_2CF_3$ and $CF_2ClCF_2CHF_2$ is produced in (1).

6. The process of claim 5 wherein $CHClFCF_2CF_3$ and $CF_2ClCF_2CHF_2$ are included in the reactants of (2).

7. The process of claim 3 wherein the product from (1) and (2) consists essentially of saturated compounds containing the same number of fluorine atoms as the respective initial starting material and contains less than 10% of olefinic co-product and product containing less fluorine than the initial starting material.

* * * * *